United States Patent [19]
Aldridge et al.

[11] 4,178,213
[45] Dec. 11, 1979

[54] FERMENTATION PROCESS FOR THE PRODUCTION OF (+)-2-(5β-N-BUTYL-4β-HYDROXY-2-OXO-TETRAHYDROFURAN-3β-YL)-2α-METHYLACETIC ACID

[75] Inventors: David C. Aldridge; Roger Bowling; John C. Swait, all of Macclesfield, England

[73] Assignee: Imperial Chemical Industries Limited, London, England

[21] Appl. No.: 864,473

[22] Filed: Dec. 27, 1977

[30] Foreign Application Priority Data

Jan. 13, 1977 [GB] United Kingdom ............... 1310/77
Mar. 14, 1977 [GB] United Kingdom ............. 10622/77

[51] Int. Cl.$^2$ ............................................ C12D 13/00
[52] U.S. Cl. ................................. 435/126; 435/933
[58] Field of Search ............................ 195/36 R, 81

[56] References Cited

U.S. PATENT DOCUMENTS 3,930,014  12/1975  Aldridge et al. ..................... 195/81

OTHER PUBLICATIONS

McCorkindale et al., Tetrahedron Letters (1968), pp. 727–730.
Roy, Ph.P. Thesis University of Glasgow, pp. 154–158 (1970).
Birch et al., Australian J. Chemistry, vol. 21, pp. 2775–2784 (1968).

*Primary Examiner*—Alvin E. Tanenholtz
*Attorney, Agent, or Firm*—Cushman, Darby & Cushman

[57] ABSTRACT

The invention concerns a fermentation process for the production of (+)-2-(5β-n-butyl-4β-hydroxy-2-oxo-tetrahydrofuran-3β-yl)-2α-methylacetic acid, which compound has useful ulcer-healing properties. The process is characterised by cultivating an organism known to produce dihydrocanadensolide, such as *Penicillium canadense*, under generally conventional conditions and then extracting the culture filtrate at a pH in the range pH 3.0–7.0 with a suitable solvent, such as ethyl acetate, and then evaporating the extract to dryness. In a preferred embodiment the extraction is carried out on the culture filtrate at pH 4.0–4.5.

12 Claims, No Drawings

FERMENTATION PROCESS FOR THE PRODUCTION OF (+)-2-(5β-N-BUTYL-4β-HYDROXY-2-OXO-TETRAHYDROFURAN-3β-YL)-2α-METHYLACETIC ACID

This invention relates to a fermentation process and, more particularly, it relates to a fermentation process for the production of (+)-2-(5β-n-butyl-4β-hydroxy-2-oxo-tetrahydrofuran-3β-yl)-2α-methylacetic acid which possesses valuable ulcer-healing properties.

The production of dihydrocanadensolide together with up to 3% w/w canadensolide by fermentation of *Penicillium canadense*, and in particular of the strain identified as No. 95493 of the Commonwealth Mycological Institute, Kew, England, in an aqueous nutrient medium, has been described in U.K. patent specification Ser. No. 1434595, the amount of canadensolide being reduced by increased fermentation times. We have now discovered, and herein lies our invention, that if the nutrient medium from such a fermentation (or from fermentation of a related organism) is solvent extracted at a pH within a specific range, then quite unexpectedly the mono-lactone (+)-2(5β-n-butyl-4β-hydroxy-2-oxo-tetrahydrofuran-3β-yl)-2α-methylacetic acid may be obtained.

According to the invention there is provided a fermentation process for the production of (+)-2-(5β-n-butyl-4β-hydroxy-2-oxo-tetrahydrofuran-3β-yl)-2α-methylacetic acid having the formula:

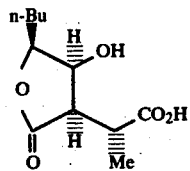

which comprises the cultivation of a dihydrocanadensolide yielding strain of a species of the genus *Penicillium* or of the genus *Aspergillus*, in an aqueous nutrient medium containing a source of assimilable carbon and a source of assimilable nitrogen, extraction of the culture filtrate at a pH from 3.0–7.0 with a substantially water immiscible organic solvent, and evaporation of the extract to dryness.

It is to be understood that the stereo-chemistry depicted in formula I is relative, and that the absolute configuration may in fact be the mirror image of that depicted. For convenience, the αβ system of representing stereochemistry is used throughout this specification and the numbering is based on 2-(2-oxo-tetrahydrofuran-3-yl)acetic acid having the formula:

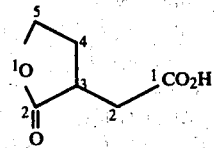

In this specification, a dihydrocanadensolide yielding strain of a species of the genus *Penicillium* or *Aspergillus* means a species of the genus *Penicillium* or *Aspergillus* which, on cultivation in an aqueous nutrient medium such as described herein, followed by extraction of the culture filtrate thereby obtained with a substantially water immiscible organic solvent, such as described herein, at a pH of less than pH 3.0, and then evaporation of the extract to dryness, yields dihydrocanadensolide.

A suitable species of the genus Penicillium is, for example, the species *Penicillium candense*, for example the strain identified as No. 95493 of the Commonwealth Mycological Institute (CMI), Kew, England, or the species *Penicillium arenicola*, for example the strain identified as No. 555.70 of the Centraalbureau voor Schimmelcultures (CBS), Baarn, Netherlands.

A suitable species of the genus Asperigillus is, for example, the species *Aspergillus terricola var. indicus*, for example, the strain identified as CBS No. 167.63.

A particularly preferred strain of a species of the genus Penicillium, however, is that referred to above identified as CMI No. 95493.

A suitable source of assimilable carbon is, for example, glucose, sucrose or molasses, of which glucose is preferred. The source of assimilable carbon is generally present in the nutrient medium at a concentration of 2 to 12% by weight and preferably at a concentration of 8 to 10% by weight.

A suitable source of assimilable nitrogen may be conveniently provided, for example, by an ammonium salt of an inorganic acid, for example, of phosphoric, hydrochloric or sulphuric acid, by an ammonium salt of an organic acid, for example, of tartaric or acetic acid, or by a source of organic nitrogen, for example a yeast extract. The source of assimilable nitrogen is generally present in the nutrient medium such that there is a concentration of 0.01% to 0.10% by weight of elementary nitrogen, and preferably 0.02% to 0.04% by weight, available in the medium.

In addition, the medium will also contain generally smaller quantities of essential elements, such as phosphorus (for example as potassium dihydrogen phosphate or diammonium hydrogen phosphate), magnesium (for example as magnesium carbonate or sulphate), sulphur (for example as a metal sulphate) and potassium (for example as potassium carbonate or chloride), together with generally still smaller quantities of one or more so called trace-elements, such as iron, copper, zinc, manganese or molybdenum, as suitable salts.

The cultivation is conveniently carried out at a temperature in the range, for example, 18°–30° C., but is preferably carried out in the range 24°–27° C.

The fermentation process may be carried out either using conventional surface culture conditions or using conventional aerated stirred culture conditions, which are preferred. When stirred culture conditions are used, the fermentation is preferably carried out for at least 7 days before filtration and extraction is carried out.

The fermentation process is preferably carried out with the pH of the nutrient medium controlled in the general range pH 4.0–5.8, and initially at or near pH 4.5, for example at pH 4.3–4.8. The pH may be conveniently controlled, for example, by external means, for example by periodic addition of a strong base such as potassium hydroxide, or by internal means, for example by inclusion of a suitable buffer, for example sodium hydrogen malate, tri-sodium citrate or sodium lactate.

Although the compound of formula I may be isolated from the culture filtrate (obtained from the fermentation broth) by extraction at a pH in the range 3.0–7.0 with a substantially water-immiscible organic solvent, a preferred pH at which to carry out the extraction of the culture filtrate is in the range, for example, pH 3.8–5.0, and especially in the range pH 4.0–4.5.

A suitable, substantially water-immiscible organic solvent is, for example, chloroform, ethyl acetate, or butyl acetate, and of these ethyl acetate is preferred. The evaporation of the extracts to dryness is preferably carried out as rapidly as possible, under reduced pressure, and at a temperature below 30° C.

As stated above the compound of formula I, which is obtainable by the process of the invention, possesses valuable ulcer healing properties. These properties may be conveniently demonstrated in a test where the compound being evaluated is dosed orally or subcutaneously daily for 21 days to rats in which duodenal ulceration has been produced by application of acetic acid to the duodenum. Ulcer healing activity is then assessed on the basis of a substantial reduction in the size or incidence of the duodenal ulcers as compared with the ulcers of an undosed control group. In this test the compound of formula I shows significant activity at a daily oral dose of 5 mg./kg., and during the period of the test no signs of overt toxicity were observed with the compound of formula I.

When used to produce an ulcer healing effect in warm blooded animals a compound of formula I is administered, preferably as a suitable pharmaceutical composition, at a daily oral or subcutaneous dose of 50mg./kg. or less, preferably from 0.25 to 5mg./kg., repeated if necessary at 4–5 hourly intervals. In man this is equivalent to a dose of 12.5–250mg., four times per day.

The invention is illustrated but not limited by the following Examples in which "Oxoid," "Cerelose" and "Gas-chrom Q" are trade-marks, and yields (where given) are purely illustrative, and are not to be construed as the maximum attainable:

EXAMPLE 1

An agar slant of nutrient medium (45ml.) was prepared comprising:

Potato extract (from 200g. of peeled and chopped potatoes boiled in one liter of deionised water for 20 minutes then strained)
Glucose ("Cerelose" brand): 20g.
Agar ("Oxoid" No. 3) 20g.
Deionised water to: 1 l.

and was sterilised by boiling for 20 minutes at 15 p.s.i. The slant was inoculated with Penicillium canadense C.M.I. 95493 (previously maintained on an agar medium containing 2.0% w/v potato extract, 2.0% w/v carrot extract and 2.5% w/v "Oxoid" agar No. 3) and incubated at 25° C. for 24 days. The mycelium and spores from the slant were rubbed off into sterile water (100ml.) and the suspension thereby obtained was added to one liter of medium containing:

D(+)-tartaric acid: 0.266% w/v
Diammonium tartrate: 2.66% w/v
Diammonium hydrogen phosphate: 0.04% w/v
Potassium carbonate (anhydrous): 0.04% w/v
Magnesium carbonate trihydrate: 0.027% w/v
Ammonium sulphate: 0.016% w/v
Zinc sulphate heptahydrate: 0.0042% w/v
Ferrous sulphate heptahydrate: 0.0042% w/v
Yeast extract ("Oxoid"): 0.10% w/v
Glucose ("Cerelose" brand): 5.0% w/v
Deionised water to: 100.0% which had been adjusted to pH 5.6 by addition of aqueous potassium hydroxide solution and then sterilised by autoclaving at 15 p.s.i. for 30 minutes. The mixture was shaken in a 2 l. conical flask, using a rotary shaker, at 200 r.p.m. for 2 days at 25° C. Two separate portions (200ml.) of the resulting broth were used to inoculate two separate portions (1 l.) of an inoculum medium A containing:

Glucose ("Cerelose" brand): 5.0% w/v
Diammonium tartrate: 0.24% w/v
Potassium dihydrogen phosphate: 0.50% w/v
Magensium sulphate heptahydrate: 0.1% w/v
Trace element concentrate: 0.2% v/v
Deionised water to: 100.0% which had been adjusted to pH 5.6 by addition of aqueous potassium hydroxide solution and had then been sterilised by autoclaving at 15 p.s.i. for 30 minutes.

The trace element concentrate contained the following ingredients:

Ferrous sulphate heptahydrate: 0.1% w/v
Cupric sulphate pentahydrate: 0.015% w/v
Zinc sulphate heptahydrate: 0.1% w/v
Manganese sulphate tetrahydrate: 0.01% w/v
Potassium molybdate: 0.01% w/v
Deionised water to: 100.0%

The resulting mixture was shaken at 200 r.p.m. on a rotary shaker for 5 days at 25° C.

The contents of the flasks were added to a 40 l. glass fermentation vessel containing 33 l. of a production medium similar to the inoculum medium A described above but with the addition of a further 5.0% w/v of glucose ("Cerelose" brand) and 0.45% w/v of sodium hydrogen malate. [The pH of the production medium had first been adjusted to 5.6 and sterilised by autoclaving, the pH after which being 5.75.]

The fermentation was carried out at a temperature of 25° C. with stirring at 410 r.p.m. and aeration at a rate of 15 l./minute. After 10 days incubation the broth was filtered and the culture filtrate pH of 5.8 was adjusted to 4.5 by addition of hydrochloric acid. A portion (15 l.) of the filtrate was then extracted with ethyl acetate (2×5 l.). The extracts were combined, dried ($Na_2SO_4$) and evaporated to dryness under reduced pressure at a temperature not exceeding 30° C. giving a semi-solid residue (37.7g.). The residue was triturated with ether (100ml.), filtered and the solid thus obtained washed with ether (2×20ml.) to give (+)-2-(5β-n-butyl-4β-hydroxy-2-oxo-tetrahydrofuran-3β-yl)-2α-methylacetic acid (10.3g.). This compound was further purified by dissolving in a minimum volume of acetone at 20°–25° C. and adding, with stirring, 5–10 times that volume of light petroleum (b.p. 60–80). The resulting pure crystalline precipitate was filtered and washed with light petroleum (b.p. 60–80) to give material m.p. 114–116° C., $[\alpha]_D^{28}$ +.77 (c, 2.5; methanol) of $R_f$ 0.45 (on silica gel 0.2 mm. plates, developed in chloroform: methanol:acetic acid 90:5:5) and having the following characteristic NMR spectrum:

| | d₆-acetone | | | | d₆-acetone + TCAI | | |
|---|---|---|---|---|---|---|---|
| Signal | $\delta$ | Type | Proton No. | Coupling Constant ($H_z$) | $\delta$ | Type | Coupling Constant ($H_z$) |
| 5β-n-butyl | 0.89–1.72 | m | 9 | | 0.90–1.72 | m | |
| 5α-H | 4.31 | dt | 1 | $J_1 = 3$ $J_2 = 7$ | 4.6 | dt | $J_1 = 3$ $J_2 = 7$ |
| 3β—C(CH₃)(H)—CO₂H | 1.46 | d | 3 | $J = 6.5$ | 1.46 | d | $J = 6.5$ |
| 3β—C(CH₃)(Ⓗ)—CO₂H | 2.86 | m | 1 | | 2.86 | dq | $J_1 = 6.5$ $J_2 = 10$ |
| 4α-H | 4.49 | dd | 1 | $J_1 = 3$ $J_2 = 4.5$ | 5.75 | dd | $J_1 = 3$ $J_2 = 4.5$ |
| 3α-H | 2.86 | m | 1 | | 3.2 | dd | $J_1 = 4.5$ $J_2 = 10$ |

Table Note

The NMR spectral data was determined at 100 MH$_z$ using tetramethylsilane as an internal reference and the conventional abbreviations for complex interactions were used, for example:

m: multiplet, d: doublet, t: triplet, q: quartet.

TCAI stands for trichloroacetyl isocyanate.

EXAMPLE 2

An agar slant of nutrient medium (45ml.) was first prepared comprising:

Potato extract (from 200 g. of peeled and chopped potatoes boiled in one liter of deionised water for 20 minutes then strained)
Glucose ("Cerelose" brand): 20g.
Agar ("Oxoid" No. 3): 20g.
Deionised water to: 1 l.

and was sterilised by boiling for 20 minutes at 15 p.s.i,. This slant was inoculated with *Penicillium canadense* CMI No. 95493; previously maintained on an agar medium containing 2.0% w/v potato extract, 2.0% w/v carrot extract and 2.5% w/v "Oxoid" agar No. 3) and then incubated at 25° C. for 20 days. The mycelium and spores from the slant were rubbed off into sterile water (100ml.) and the suspension thereby obtained was added to one liter of an inoculum medium having the same composition as the inoculum medium A in Example 1, and which had been previously adjusted to pH 5.6 by addition of aqueous potassium hydroxide solution and then sterilised by autoclaving at 15 p.s.i. for 30 minutes. The mixture obtained was then shaken at 200 r.p.m. on a rotary shaker for 7 days at 25° C.

Two such portions of the inoculum mixture thereby obtained were added to a 40 l. glass fermentation vessel containing 33 l. of a production medium similar to the inoculum medium A described in Example 1, but containing an additional 5.0% w/v of glucose ("Cerelose" brand) and 0.45% w/v of sodium hydrogen malate. [The pH of the production medium had been previously adjusted to 5.6 and then sterilised by autoclaving, the pH after which being 5.5.]

The fermentation was carried out at a temperature of 25° C. with stirring at 410 r.p.m. and aeration at a rate of 15 l./minute. After 14 days incubation the broth was filtered and the culture filtrate pH of 5.3 was adjusted to 4.0 by addition of hydrochloric acid. The filtrate (12.5 l.) was then extracted with ethyl acetate (2×6 l.). The extracts were combined, dried (Na₂SO₄) and evaporated to dryness under reduced pressure at a temperature not exceeding 30° C. giving a semi-solid residue. This residue was triturated with ether (60ml.), filtered and the solid thus obtained was washed with ether (2×20ml.) to give (+)-2-(5β-n-butyl-4β-hydroxy-2-oxo-tetrahydrofuran-3β-yl)-2α-methylacetic acid (10.4g.), identical with the material isolated in Exaple 1 as judged by IR and NMR spectroscopy and TLC comparison.

EXAMPLE 3

An inoculum of *Penicillium canadense* (CMI No. 95493) was prepared as described in example 2. A portion (500ml.) of this inoculum was added to a 14 l. glass fermentation vessel containing 12 l. of a production medium containing:

Glucose "Cerelose" brand: 10% w/v
Diammonium tartrate: 0.24% w/v
Potassium dihydrogen orthophosphate: 0.50% w/v
Magnesium sulphate heptahydrate: 0.10% w/v
*Trace element concentrate: 0.20% v/v
Deionised water to: 100%.

[*Identical composition to that used in Example 1].

[The pH of this medium had been adjusted to 5.6 by addition of aqueous potassium hydroxide solution and had then been sterilised by autoclaving at 15 p.s.i. for 30 minutes.]

The fermentation was carried out at a temperature of 25° C. with stirring at 410 r.p.m., and aeration at a rate of 6 l. /minute. During the first five days of the fermentation the pH was maintained at 4.3–4.6 by automatic addition of aqueous potassium hydroxide solution controlled on demand by a pH-meter. Thereafter the pH was allowed to rise so that after 14 days incubation, the pH of the broth was 5.1. The broth was then filtered to give a culture filtrate (C) (6.5 l.).

A portion (6.0 l.) of filtrace C was adjusted to pH 4.0 by addition of hydrochloric acid and then extracted with ethyl acetate (2×3l.). The combined extracts were dried (Na₂SO₄), and evaporated to dryness under reduced pressure at a temperature at or below 30° C. The semi-solid residue obtained was triturated with ether ( b 60ml.). The mixture was filtered and the solid thus obtained was washed with ether (2×20ml.) to give (+)-2-(5β-n-butyl-4β-hydroxy-2-oxo-tetrahydrofuran-3β-yl)-

2α-methylacetic acid (6.2g.) identical with that obtained in Example 1, as judged by IR and NMR spectroscopy and TLC comparison.

EXAMPLE 4

A portion (500ml.) of the culture filtrate C obtained in Example 3 was extracted at various pH values and the quantity of (+)-2-(5β-n-butyl-4β-hydroxy-2-oxotetrahydrofuran-3β-yl)-2α-methylacetic acid (B) obtained estimated by GLC following its conversion to the bis(-trimethylsilyl)derivative, using the following procedure:

An aliquot of filtrate C (50ml.) (from Example 3) was adjusted to a particular pH and extracted twice with ethyl acetate (30ml., then 15ml., shaking for 1 minute with each portion). The combined extracts were dried ($Na_2SO_4$, 10g.) and filtered. The residue was washed with ethyl acetate (5ml.) and the combined filtrate and washings were made up to a volume of 50ml. with further ethyl acetate. An aliquot (50μl.) of this solution was removed and mixed with analytical grade pyridine (100μl.) and a portion (50μl.) of a freshly prepared 10% v/v solution of trimethylchlorosilane in bis(trimethylsilyl)-acetamide was added. After 1 hour at 20°–25° C. this mixture was assayed for the bis(trimethylsilyl) derivative of B by Gas Liquid Chromatography, A, using a glass column (1.5m×4 mm.) containing silicone gum rubber, type E 301 (available from Phase Separations Ltd., Queensferry, Flintshire, U.K.) coated onto the particulate diatomaceous support known as "Gas-chrom" Q (80–100mesh) (available from Field Instruments Ltd., Orchard Road, Richmond, Surry, U.K.), at a temperature of 245° C. and a nitrogen flow rate of 60ml./minute employing a flame ionisation detector in a Pye Unicam Series 104 Gas Chromatograph (available from Pye Unicam Ltd., Cambridge, U.K.). Under these conditions, the bis(trimethylsilyl) derivative of B has a retention time of 2.00 minutes.

Using the above procedure, the following quantities of B were shown to have been extracted from the culture filtrate C at particular pH values:

| pH  | mg. of B/litre of C |
|-----|---------------------|
| 7.0 | 18                  |
| 6.5 | 89                  |
| 6.0 | 122                 |
| 5.5 | 316                 |
| 5.0 | 684                 |
| 4.5 | 663                 |
| 4.0 | 1275                |
| 3.5 | 1357                |
| 3.0 | 1263                |

EXAMPLE 5

An agar slant of nutrient medium (prepared as in Example 1) was inoculated with *Penicillium arenicola* (CBS No. 555.70) and incubated at 25° C. for 12 days. The mycelium and spores from the slant were rubbed off into sterile water (100ml.). A portion (5ml.) of this suspension was added to a 500ml. conical flask containing 100ml. of the production medium described in Example 1. The flask was incubated at 25° C. on a rotary shaker.

After 14 days, the broth was filtered and the culture filtrate was adjusted to pH 4.0 by addition of hydrochloric acid. The filtrate was then extracted with ethyl acetate (2×20ml.). The extracts were dried and evaporated as described in Example 1, 2 and 3 to give solid material which yielded (30)-2-(5β-n-butyl-4β-hydroxy-2-oxo-tetrahydrofuran-3β-yl)-2α-methylacetic acid identical with that obtained in Example 1, as judged by IR and NMR spectroscopy and TLC comparison.

What we claim is:

1. A fermentation process for the production of (+)-2-(5β-n-butyl-4β-hydroxy-2-oxo-tetrahydrofuran-3β-yl)-2α-methylacetic acid having the formula:

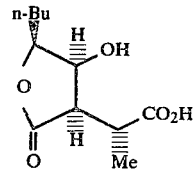

which comprises cultivating a dihydrocanadensolide yielding strain of a species of the genus Penicillium or of the genus Aspergillus, in an aqueous nutrient medium containing a source of assimilable carbon and a source of assimilable nitrogen, isolating the compound of formula I by extracting the culture filtrate at a pH from 3.8–5.0 with a substantially water immiscible organic solvent, and evaporating the extract to dryness.

2. A process as claimed in claim 1 wherein a strain of the species *Penicillium canadense, Penicillium arenicola 1* or *Aspergillus terricola var. indicus* is cultivated.

3. A process as claimed in claim 2 wherein the strain of *Penicillium canadense* is that identified as CMI No. 95493, the strain *Penicillium arenicola* is that identified as CBS No. 555.70, and the strain of *Aspergillus terricola var. indicus* is that identified as CBS No. 167.63.

4. A process as claimed in claim 1 wherein the strain of *Penicillium canadense* is that identified as CMI No. 95493.

5. A process as claimed in claim 1 wherein the extraction is carried out at a pH in the range pH 4.0–4.5.

6. A process as claimed in claim 1 wherein the pH of the nutrient medium is controlled at a pH in the general range pH 4.0–5.8.

7. A process as claimed in claim 1 wherein the pH of the nutrient medium is initially controlled at pH 4.3–4.8.

8. A process as claimed in claim 6 or 7 wherein the pH of the nutrient medium is controlled by periodic addition of a strong base.

9. A process as claimed in claim 6 or 7 wherein the pH of the nutrient medium is controlled by inclusion of a suitable buffer in the said medium.

10. A process as claimed in claim 9 wherein the buffer is sodium hydrogen malate, tri-sodium citrate or sodium lactate.

11. A process as claimed in claim 1 wherein the source of assimilable carbon is glucose, sucrose or molasses and is present in the nutrient medium at a concentration of 8–10% by weight.

12. A process as claimed in claim 1 wherein the source of assimilable nitrogen is an ammonium salt of phosphoric, hydrochloric, sulphuric, tartaric or acetic acid, or a yeast extract, and is present in the nutrient medium such that there is a concentration of 0.02–0.04% by weight of elementary nitrogen available in the medium.